US006612156B1

(12) United States Patent
Hakimuddin (10) Patent No.: US 6,612,156 B1
(45) Date of Patent: Sep. 2, 2003

(54) ACOUSTIC MIXING AND MEASUREMENT SYSTEM AND METHOD

(75) Inventor: Mustafa Hakimuddin, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/003,834

(22) Filed: Oct. 25, 2001

(51) Int. Cl.[7] .......................... G01N 15/00; G01H 5/00
(52) U.S. Cl. ........................... 73/61.75; 73/597
(58) Field of Search ............... 73/61.75, 61.48, 73/597; 210/739, 85, 94

(56) References Cited

U.S. PATENT DOCUMENTS

| | | | | |
|---|---|---|---|---|
| 4,671,102 A | * | 6/1987 | Vinegar et al. | 73/61.48 |
| 5,253,529 A | * | 10/1993 | Lenormand et al. | 73/597 |
| 5,948,271 A | * | 9/1999 | Wardwell et al. | 210/739 |

OTHER PUBLICATIONS

Sheen et al, Cavitation Controlled Ultrasonic Agitator, 1989, IEEE Ultrasonics Symposium, pp 653–656.*
Tejinder et al, Control of Crystal size and Distribution of Zeolite A, Ind. Eng. Chem. Res., 40(4) 1133–1139, 2001,.10.1021.*
Ultrasonic Crystalliser, Process Eng. (Londor) 1974, p 137.*
Law et al, Applications of High/Low–Frequency Ultrasonic Energy for Break–Up of Oil Field Emulsions, 7th Unitar Heavy Crude & Tar Sands Int Conf (Beijing, China, Oct. 27–30, 1998, Proc 1998 (Pap 1998 018).*
Genck et al, Sonocrystallization, CEP Magazine, Sep., 2001.*
McCausland, Use the Power of Sonocrystallization for Improved Properties, CEP, Jul. 2001, pp. 56–61.*
SPE 58729, "High Pressure Crystallization of Deep–Water Completion Brines" (Feb. 2000).

* cited by examiner

Primary Examiner—Helen Kwok
Assistant Examiner—J L Politzer
(74) Attorney, Agent, or Firm—Loren G. Helmreich; Browning Bushman, P.C.

(57) ABSTRACT

An acoustic measurement system detects solids within a fluid includes a sample cell 10 for containing the fluid, a first transducer 20 for outputting a first acoustic detection signal at a first frequency, a first acoustic receiver 20 responsive to the first acoustic detection signal, and a second acoustic transducer 20 for outputting an acoustic second mixing signal at a second frequency to mix the solids in the fluid within the sample cell. Controller 40 may vary the "on" time of the second transducer with respect to the measurement of the first acoustic signal. The fluid within the cell may be tested under a wide range of temperatures and pressures. The acoustic measurement system may also be used to measure the bulk modulus of the liquid. The method of the invention allows for the detection of crystallization for a portion of the fluid in the sample cell under widely varying conditions.

20 Claims, 4 Drawing Sheets

ACOUSTIC MIXING AND MEASUREMENT SYSTEM AND METHOD

FIELD OF THE INVENTION

The present invention relates to an acoustic measurement system and method suitable for detecting solids in a fluid. More particularly, this invention relates to an improved acoustic mixing system which is able to detect the presence of various solids in a drilling fluid, and/or to measure the bulk modulus of the fluid, to provide valuable information relative to the drilling or production operation.

BACKGROUND OF THE INVENTION

Acoustic measurement devices provide an excellent tool for the detection of solids in fluid systems, and may be particularly useful where the presence of the solids may pose problems to other measurement devices. Acoustic measurements may be utilized to detect the presence and/or occurrence of waxes, paraffins, asphaltenes, hydrates, and crystalline compositions within a fluid media. These measurements thus provide valuable information to, for example, an oil service company interested in drilling and/or production of oil from a subterranean formation. To improve measurement/determination accuracy and reliability, the fluid phases in a sampled media to be measured preferably may be stirred within the sample cell, substantially while making measurements, to suspend and disperse solid phases within the fluid phases. However, the accuracy of existing acoustic detection devices and methods are hampered by lack of adequate means for mixing a sample during detection measurements. The ineffectiveness of prior art approaches that have attempted to effectively mix samples within acoustic detection devices is illustrative of the problem.

One attempt to induce mixing has been to rock or otherwise rotate or move the sample cell. Studies have determined, however, that the mixing action achieved by such methods frequently may not provide appreciable measurement signal change as compared to a non-rocked measurement, and thereby does not sufficiently increase measurement accuracy. Such rocking or dynamic mechanism also may be cumbersome and may require special care for the tubings and electrical connections interconnected with the sample cell. Other mixing attempts have included providing a specially designed ring inside of the sample cell that could move inside of the cell while rocking the cell, thereby generating mixing within the cell. Mixing results generated by the ring device may also be inadequate. The ring also offers an increased opportunity for measurement signal distortion if the ring becomes cocked or wedged in the cell. The ring may also be deficient in introducing mixing action within the pores of a porous test media.

Other mixing techniques have included providing a mechanical stirrer inside of the measurement cell, which may in some instances result in improved mixing results as compared to rocking type mixing devices. Mechanical mixing devices, however, may increase the complexity and size dimensions of the measurement cell. In addition, invasive type mixing devices may create measurement distortions, undesirable sample disturbances, and may interfere with measurement results. Additional avenues for the occurrence of leaks at high pressures may also be included. Measurement apparatus and cell construction, fabrication, operation, expense, portability and versatility may also present additional problems and challenges with mechanical and other invasive type mixing devices, particularly for operations across a wide temperature and/or pressure spectrum.

The disadvantages of the prior art are overcome by the present invention, and an improved acoustic measurement device and method is hereinafter disclosed for reliably mixing materials within a measurement cell in order to more accurately detect the presence of solids within a fluid media, and/or to measure the bulk modulus of a fluid.

SUMMARY OF THE INVENTION

The present invention provides a method and system for more effectively mixing fluid media samples in an acoustic measurement cell to facilitate detection of solids in the fluid, or to measure the bulk modulus of the fluid. This invention is particularly applicable in measurements to detect the presence of waxes, paraffins, asphaltenes, hydrates and crystalline solids within the fluid, which may then provide valuable information to an oil or gas well drilling and/or production operation. More particularly, this invention may detect the presence of such solids in the rather unusual conditions of low temperature and high pressure, such as may be encountered in an offshore, deep-water environment. The invention may also be used to measure the bulk modulus of a pressurized fluid, thereby providing valuable information regarding the mixture of liquids and gas under high pressure conditions. System adaptability and portability render the invention highly flexible and easily upgradable, even for higher pressures and lower temperature than may be encountered in offshore, deep-water environments, such as in down-hole applications, geothermal applications, and in industries other than analysis of well fluid. The term "fluid" as used herein is intended to include Neutonian and non-Neutonian fluids, emulsions, gas-liquid mixtures, and fluids in the presence of solid media, such as within the pores of a rock sample.

It is an object of the present invention to provide an acoustic measurement system for detecting solids in the fluid, or for measuring the bulk modulus of the pressurized fluid, with the system including a sample cell for containing the fluid and a first acoustic transducer for outputting a first acoustic detection signal of a first frequency, and an ultrasonic receiver responsive to the first acoustic detection signal. A second acoustic transmitter is provided for outputting an acoustic second mixing signal at a second frequency to mix the solids in the fluid within the sample cell.

According to the method of the invention, ultrasonic measurements may be obtained under a variety of pressure and temperature conditions within a cell, with the frequency of the second ultrasonic mixing signal being significantly different than the frequency of the first acoustic detection signal. In an exemplary embodiment, the frequency of that first signal may between 500 kHz to 1 gHz, while the second signal may be 50 kHz or less.

It is a feature of the present invention that the ultrasonic measurement system is capable of simulating downhole conditions, and may be used to differentiate between a gas pocket and hydrate to determine how much hydrate is present, the size distribution of the solid particles within the fluid, and the kind of hydrate, e.g., methane or pentane.

It is a further feature of the invention that the first acoustic detection signals may be generated with both a longitudinal and a shear wave transducer.

Yet another feature of the invention is that the ultrasonic measurement system is able to measure the acoustic velocity of samples at various temperatures and pressures. Components of the samples may be one of multiple phases during measurement tests.

A further feature of the invention is that controller may be provided for regulating the "on" time of the second transducer, and for detecting the first acoustic detection signals during "off" time of the second transducer.

Another feature of the invention is that the acoustic measurement system is able to reliably test fluids with fluid pressures in excess of 20,000 psi.

An advantage of the present invention is the ultrasonic measurement system may be used to calibrate sonic logs, or to differentiate between hydrates, gas pockets, shallow water flow zones, and other phenomenons.

It is a further advantage of the invention that the ultrasonic measurement system may be used to detect wax, asphaltene, crystallization, and/or hydrate.

A significant advantage of the method of the invention is the significantly reduced time required to conduct reliable measurements, along with the versatility when testing the fluid under various pressure and temperature conditions.

These and further objects, features, and advantages of the present invention will become apparent from the following detailed description, wherein reference is made to the figures in the accompanying drawings.

DETAILED DESCRIPTION OF PREFERRED EMBODIMENTS

Figure 1:
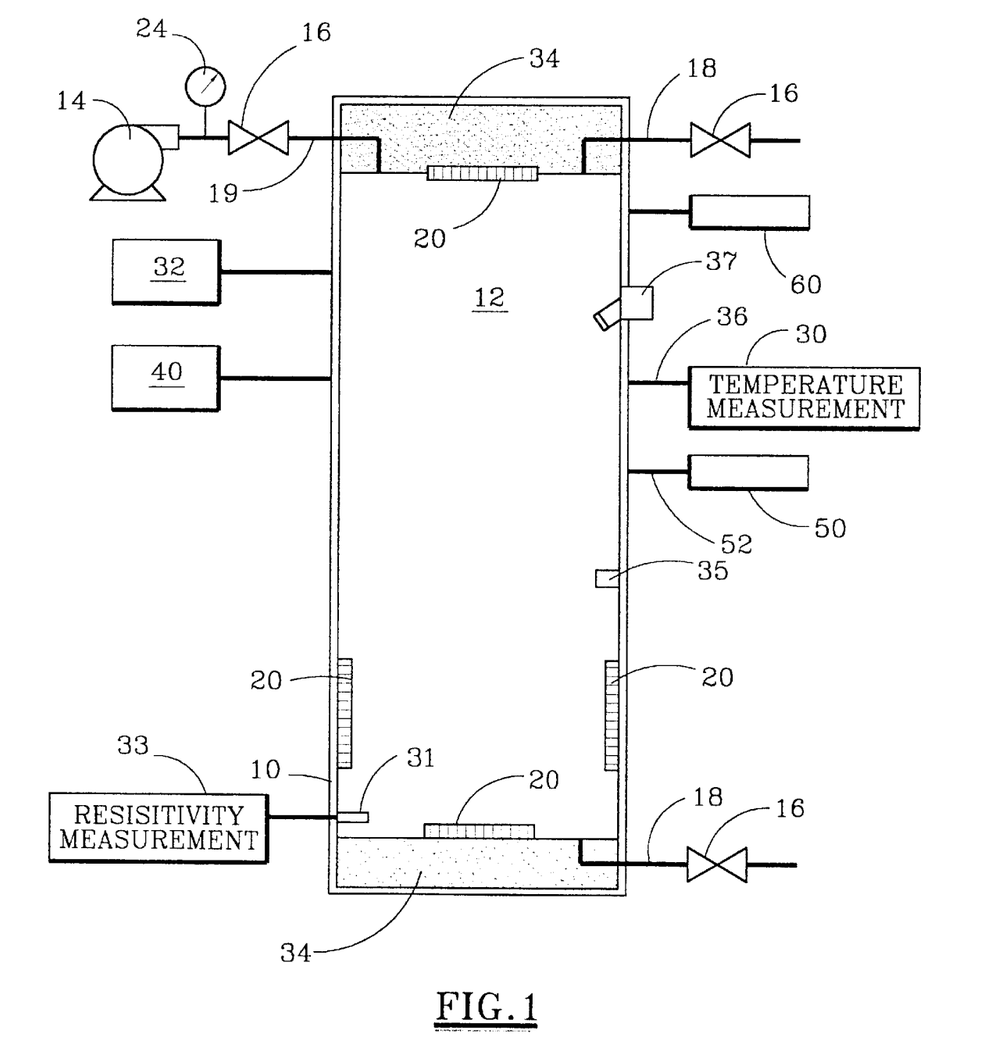
FIG. 1 illustrates one embodiment of the acoustic mixing system according to the present in invention.

FIG. 1 illustrates a suitable embodiment of a system according to this invention. A first frequency range of acoustic energy signal may be utilized to perform a measurement/detection function of the system, while a second frequency range of acoustic energy signal may be utilized to perform the mixing operation. Although each signal may be selected to be substantially different frequencies, each signal may be ultrasonic signal. An intermittent pulse or a continuous application of the mixing acoustic energy may non-invasively generate significant amounts of mixing action through eddy current propagation throughout the cell and/or the sample media.

Acoustic detection may be defined as the generation, transmission, and reception of energy in the form of vibration waves in matter. Acoustic waves travel through different media, such as solid, liquid and gas, with different velocities when the internal properties of the media are fixed. When internal properties of the media change, the velocity of the acoustic wave passing through that media changes. Therefore, the acoustic velocity change may be used to detect the solid phase, e.g. crystal, appearing in the brine solution being tested under a given pressure. The acoustic velocity change may also be used to measure the bulk modulus of a well-mixed pressurized fluid, so that the gas content of the mixture may be accurately determined relatively quickly.

The acoustic measurement/detection frequency may be a high ultrasonic frequency signal, such as from 500 kHz to in excess of 100 MHZ, and even as high as one gHz. The mixing acoustic energy may be a relatively lower ultrasonic frequency, such as 50 kHz or less, and preferably less than 25 kHz. For example, the ultrasonic mixing method and system may utilize an ultrasound device that operates at approximately 20 kHz. The mixing acoustic frequency and energy may be selected and/or adjusted, such that the mixing acoustic energy may not interfere with or may be properly accounted for in the measurement/detection testing operation. For example, the mixing energy may be applied within the cell in an optimized series of "on-off" pulses. Thereby, measurement/detection type operations may be conducted during "off" pulse periods. In addition, pulsing the mixing energy may also reduce heat generation introduced into the sample through the acoustic energy and/or the mixing action, thereby providing an improved substantially isothermal and/or thermally controlled measurement environment.

The mixing acoustic energy may be applied within the measurement cell 10 by positioning either of a measurement/detection signal transducer and/or a mixing signal transducer 20 flush with an internal wall of the cell. Both longitudinal and shear wave transducers may be provided. Thereby, each transducer may propagate acoustic energy from a transducer within the cell. If desired, the transducers may be transceivers which both receive an electrical signal to output an acoustic signal, and receive the acoustic signal to output an electric signal to the data acquisition system. One or more of the transducers may also be positioned substantially adjacent an internal surface of the cell. In an alternate embodiment, one or more of the transducers may be secured to an external surface of the cell, whereby acoustic energy may be propagated at least partially through a cell wall. If desired, the position of each transducer with respect to the cell may be adjusted to optimize detection and mixing. Either embodiment may facilitate a minimal or non-invasive propagation of mixing energy, so as to reduce the probability of a transducer interfering with measurement/detection. The acoustic delay time, the refraction of the acoustic wave, the reflection of the acoustic wave and/or the change in amplitude of the acoustic signal may be monitored to detect solid particles in the fluid.

Further, due to the substantially noninvasive and substantially non-mechanical mixing action, the methods and systems of this invention may be effectively applied at pressure ranges in excess of pressure limits which may be applicable to prior art mixing systems. As pressure increases, the viscosity of a sample fluid may also increase, which may thereby reduce the effectiveness of a mixing system for a particular level of mixing energy. As pressure increases in a sample which is mixed according to this invention, additional power may be applied to the transducer or horn 20. The amount of power required may be dependent upon variables including sample/cell size, number of horns, fluid viscosity, and temperature and pressure. For example, a particular fluid may require less than 50 watts of power from an amplifier to mix at a first pressure, and that same fluid may require 400 watts of power at much higher pressures, such as 15,000 to 20,000 psi. Other fluids and fluid properties may require even more power. Measurements of the bulk modulus of the fluid may be made at pressures in excess of 5000 psi. The mixing techniques of the present invention allow reliable measurements to be taken much more rapidly than when using prior art mixing techniques.

Table 1 summarizes some of the advantages and disadvantages of the various prior art detection systems and the system according to this invention. As illustrated in Table 1, a rocking type mixing system substantially may be effective for pressures of less than 100 psi. Rocking the cell while also mechanically stirring cell contents, such as with a stirring ring, may only be moderately effective at pressures in excess of 1000 psi and may be substantially ineffective for pressures in excess of 2000 psi. The methods and systems of this invention may be effective for pressures from less than 10 psi to very high pressures, including pressure in excess of 15,000 psi and pressures above 20,000 psi.

| Wax/Asphaltene Detection Method | Sample Mixing Mechanism | Mixing Mechanism Effectiveness | Effective Pressure Range |
|---|---|---|---|
| Acoustic Velocity/ Resonance measurement | Rocking the Acoustic Cell | Negligible | Ineffective for 100 psi–20,000 psi |
| Acoustic Velocity/ Resonance measurement | Rocking the Cell with a Stirring Ring | Moderate | 10 psi–2000 psi only. Ineffective for pressure above 2000 psi |
| Acoustic Velocity/ Resonance measurement | Ultrasonic Mixing | Very Effective | 10 psi–20,000 psi |

Likewise, the methods and systems of this invention may be effectively applicable to temperature ranges in excess of temperature range limits of prior art systems. Ultrasonic mixing according to the methods and system of this invention may be effectively achieved in fluid media from −30 degrees F to in excess of 300 degrees F.

A system for practicing the present invention may facilitate acoustic mixing of a sample media by providing a cell 10 with at least one mixing transducer or horn 20. Measurement/detection may be conducted with at least one and preferably two additional transducers 20, as illustrated in FIG. 1. The measurement/detection transducers 20 may be capable of transmitting and receiving compressional and/or shear waves through the sample. Thereby, one or more compressional and/or shear wave receiver transducers may measure acoustic signal reflection, refraction, arrival time and amplitude. Such measurement/detection may be conducted intermittently with or substantially continuously with an acoustic mixing signal.

The measurement transducers 20 may be positioned or arranged within the cell in substantially any number of arrangements, and likewise one or more mixing transducers or horns 20 may be positioned in any number of accommodating arrangements. Thereby, the transducers 20 may be moveably positioned for distance and location to adjust the position and angle at which an acoustic wave is transmitted, encountered and/or received.

The volume 12 within the measurement/detection cell 10 also may be of a convenient size, such as from less than 1 cc to 250 cc and higher. For example, one rather commonly used cell has a volume of approximately 35 cc. The mixing acoustic signal may be preferably switched between "on" and "off" at selected intervals, such as from 0.1 seconds "on" to 0.1 seconds "off." The "on" period may be extended to in excess of an hour and an "off" period may be extended to in excess of a minute.

A programmable computer or other controller 40 may be included to control or regulate the measurement/detection operation and system. Waveform data may be captured and transferred to the computer system for analyzing the data for timing, delays, amplitude changes, and latter arrival and frequency analysis. Measurement, detection and/or analysis may be performed in substantially real time, in either the laboratory or in the field, so as to provide information which may be useful in controlling other devices, operations or processes, such as oil well production equipment, downhole tools, flow lines, and product transmission. The data acquisition system 40 may also substantially monitor and/or regulate temperature, pressure and/or volume changes of the sample in addition to collecting and/or analyzing acoustic data. State of the art temperature, pressure and volume monitoring and control systems and equipment may preferably be included to detect and/or control subtle variations therein.

The methods and systems of this invention may simulate downhole pressure, temperature and fluid conditions in a well bore, and/or formation. A rock or sand sample, either crushed or substantially in-tact, such as from a core, may be placed within the cell for acoustic measurement/detection of solids in the liquids. Thereby, a number of determinations may be made, including: (1) identification of hydrate/solid formation points and differentiating between a gas pocket and a hydrate, (2) the rate and/or amount of hydrates/solids formed under a particular set of conditions, (3) size distribution of the hydrate/solid particles, and/or (4) hydrocarbon composition of the hydrates, such as percentage of methane, ethane, or other hydrocarbon, and/or (5) the bulk modulus of the properly mixed and pressurized fluid.

The methods and systems of this invention may be integrated within a measurement/detection system at a drill rig site for detection of hydrate and/or crystallization formation in association with the mud system, such as the precipitation of salt crystals. Formation of waxes, asphaltenes and paraffins may also be detected at drilling installations, production handling facilities and in pipelines.

The methods and systems of this invention may be incorporated within a downhole tool for use in a well bore, or in another on-site usable installation system, such as in a pipeline or production facility. Thereby, acoustic measurement/detection testing may be performed in real time, and/or substantially continuously with regular or intermittent sampling and testing. A downhole sampling and testing tool may integrate the methods and systems of this invention to facilitate testing a precisely selected down-hole sample under in-situ conditions.

Information determined by the methods and systems of this invention may be utilized to calibrate sonic logs for differentiating between various formation and downhole phenomenon such as hydrate formation, gas pocket identification and water zones, such as identification of shallow water-flow zones. Acoustic travel times in a particular rock matrix also may be determined.

The methods and systems of this invention may include additional instrumentation to accommodate additional measurement and/or testing. A resistivity probe 31 may be provided which accommodates the high pressures and/or temperatures, such that resistivity measurements of a sample may be conducted substantially simultaneously with acoustic measurements. Signals from the resistivity measurement circuit 33 may be output to the data acquisition system 40. Such information may also be useful in verifying the acoustic data. In addition, near infrared spectroscopy may also be provided with sensor 35 in the cell to perform measurements, such as light absorption and scattering effects. A video camera 37 may be positioned within the cell to provide visual observation of phase changes and light scattering. Acoustic measurements may be made of a sample's liquid bulk modulus at pressures up to 20,000 psi and at temperatures from −30 degrees F. to 300 degrees F.

An acoustic cell according to this invention may also be used merely as a high pressure mixing system or device for use with non-acoustic testing/measurement/detection. The system may be utilized for mixing various combinations of oil, gas and/or water to simulate downhole phase combinations. Samples may be of a single phase, such as a gas, a liquid or a solid, or samples may be multi-phase, such as combinations thereof, including liquid-liquid and gas-gas, emulsions, and suspensions.

In other embodiments, a cell according to this invention may be utilized in the absence of acoustic mixing, or with the horn temporarily removed and a mechanical or other agitation device provided. Acoustic testing may include only one high frequency test, whereby only a shear or a longitudinal transducer is provided. The resistivity probe may be utilized alone. Temperature may be measured to observe a change in temperature that may be indicative of hydrate precipitation or crystallization. Further, a change in volume may be measured or observed to predict a phase change in the sample, such as hydrate formation or asphaltene precipitation.

FIG. 1 illustrates a suitable embodiment for an acoustic measurement system employing an acoustic mixing system. A sample cell 10 may be provided, including an interior sample chamber 12 for the placement of a sample therein for testing. An acoustic transducer 20 may be provided within the cell 10, or otherwise in acoustic communication with the chamber 12. In one embodiment, a first acoustic transducer 20 may be required for generation of an acoustic signal and a second acoustic transducer 20 may be required for receiving the generated signal. FIG. 1 illustrates an arrangement of four transducers 20.

The cell 10 may include one or more inlets 18, 19 and respective inlet valves 16 to regulate the application and reduction of pressure in the chamber 12. Inlets 18 may be included for circulating fluids into and from within the chamber 12 of the cell 10. Pumps 14 may apply fluid pressure within the cell 10, which may be recorded by a pressure recorder 24. Filters 34 may be included to prevent the migration of test media into an inlet 18, 19. A temperature control device 32 may regulate temperature within the chamber 12. A temperature measurement device 30, such as a thermocouple, may be provided with a temperature probe thermowell 36 to measure/record/indicate temperature in the chamber 12. The controller 40, such as a computer, may be connected to the transducers 20, the pumps 14, the temperature control device 32, the temperature measurement device 30, and the pressure recorder 24, as well as to the resistivity probe 31, the infrared spectroscopy sensor 35 and, if desired, the camera 37.

An adjustable acoustic transducer controller 50 may be included to provide the acoustic mixing energy to the one or more mixing transducers or horns 50 within the cell 10. The mixing energy may be transmitter into the cell 10 through an acoustic mixing energy interface 52. The acoustic mixing transducer 50 may be a low frequency adjustable ultrasonic stirring mechanism, such as may operate at 20 kHz. One or more optional devices 60 may be interconnected with the cell 10, such as a resistivity probe or device, a video camera, infrared spectroscopy equipment, or fiber optic equipment.

An experiment was conducted to measure speed of sound (SOS) through oil, brine and gas along with the effect of dissolved gas on oil and brine solution. The test was conducted using a state of the art acoustic cell setup. The test procedure involved the following: (1) Measure SOS of brine saturated with gas at 50EC and 1, 50, and 100 bar; (2) Measure SOS of dead oil at 100 bar and 50, 70, 90° C.; (3) Saturate oil at 50° C. with synthetic gas to bubble points of 50, 75, and 100 bar and measure SOS of each mixture at 50° C. and 100 bar; (4) Use oil saturated at 50° C. and 100 bar in step 3 and measure SOS at 60° C. and 40° C. and at a pressure high enough to ensure single phase; (5) Lower pressure of mixture in step 4 and measure SOS of oil phase at 50° C. and 75, 50, and 1 bar; (6) Equilibrate synthetic gas with oil at 50° C. and 100 bar and measure SOS of gas phase.

The acoustic cell was cleaned using toluene, methanol and DI water, followed by air to dry. The cell was flushed with test sample twice before SOS measurements were conducted. Brine sample was tested first. Brine was introduced from the bottom end of the acoustic cell and was purged out from the top end of the cell. SOS for the brine was measured at temperature and pressure with no gas in the cell. Gas was then injected in the cell and mixed with the brine solution using 20 kHz sonic horn at various pressure. SOS was monitored continuously while brine and gas were mixed and data was recorded when the SOS signal reached equilibrium, implying no more gas was getting mixed in the brine. Same procedure was followed for measuring SOS through oil and gas samples. Table 2 shows the results of the experiment.

TABLE 2

| Description | Hydrostatic Pressure (bar) | Temp (° C.) | Speed of Sound (m/s) |
|---|---|---|---|
| No gas (brine only) | 1 | 50 | 1544.89 |
| No gas (bring only) | 34.5 | 50 | 1552.08 |
| Introducing gas (no mix) | 50 | 50 | 1555.15 |
| Brine saturated with Gas at 50 bar and 50° C. | 50 | 50 | 1542.69 |
| Bring saturated with Gas at 100 bar and 50° C. | 100 | 50 | 1550.25 |
| Dead Oil | 100 | 50 | 1270.45 |
| Dead Oil | 100 | 70 | 1203.06 |
| Dead Oil | 100 | 90 | 1140.34 |
| Dead Oil saturated with Gas at 50 bar and 50° C. | 100 | 50 | 1194.23 |
| Dead Oil saturated with Gas at 75 bar and 50° C. | 100 | 50 | 1155.91 |
| Dead Oil saturated with Gas at 100 bar and 50° C. | 100 | 50 | 1119.32 |
| Dead Oil saturated with Gas at 100 bar and 50° C. | 100 | 40 | 1156.07 |
| Dead Oil saturated with Gas at 100 bar and 50° C. | 100 | 60 | 1083.41 |
| Dead Oil saturated with Gas at 100 bar and 50° C. | 75 | 50 | 1131.34 |
| Dead Oil saturated with Gas at 100 bar and 50° C. | 50 | 50 | 1157.31 |
| Dead Oil saturated with Gas at 100 bar and 50° C. | 1 | 50 | 1210.68 |
| Gas saturated with Oil at 100 bar and 50° C. | 100 | 50 | 925.10 |

For brine solution with no gas added, the speed of sound increases with increasing pressure at constant temperature. After introducing gas at 50 bar without mixing, the SOS of the brine increased from that at 34 bar due to the pressure increase. When the gas is mixed at 50 bar, the SOS of brine reduced a little bit, showing the effect of gas. At 100 bar, the SOS for gas saturated brine decreased, implying that the effect of gas saturation is less than that of pressure increase.

For dead oil, SOS decreased as temperature increased at 100 bar. Similarly, SOS decreased as more and more gas was mixed in the oil at 50° C. The effect of temperature on gas saturated oil also shows the same pattern as dead oil; the SOS decreased as temperature increased at 100 bar. As the pressure on the gas saturated oil was removed at constant temperature of 50° C., SOS increased with reducing pressure. The SOS through the gas saturated oil is much lower than that of brine and dead oil. The sonic mixing horn along with the ultrasonic detection transducer is a successful combination.

According to the prior art, the mixing of oil-gas and brine-gas system usually takes weeks and 100 times the size of the sample required. The solvent liquid phase is placed in a 2 liter (2000 cc) cylinder and pressurized using the solute gas. Then the sample is rocked for 24 hours and pressure drop due to mixing is observed. If there is a pressure drop, more gas is injected in the system and rocked again for 24 hours. This process is continued until there is no more pressure drop in 24 hours, implying that solvent is completely saturated with the gas. To measure the speed of sound through the sample, the sample has to be transferred in an acoustic measurement cell. This process is cumbersome and frequently takes weeks or months to bring the mix to equilibrium. Also, the only sound velocity measurements conducted are on the virgin sample and the final mixed sample. No intermediate velocity measurements can be done during the mixing phase.

The acoustic method of the present invention provides quick and controlled mixing. The sample is comparatively small and may take far less time than the prior art mixing methods. The test may be setup and finished in one day and data can be collected not only for initial and final mixing, but also for the intermediate steps. Also, the same sample may be subjected to various temperature, pressure and gas concentration tests. An important point to note is that the size of the sample is much smaller than for the prior art methods. The size is important because it costs millions of dollars to collect the live oil sample during exploration wells, startup and intermediate sampling after the well is online. An additional enhancement to the acoustic mixing system and method of this invention is the ability to detect the mixing profile during solvent flooding of oil saturated cores for oil recovery purposes and during secondary recovery operations on previously abandoned wells.

Another test was conducted to determine the brine crystallization temperature at different pressures by acoustic velocities. The velocities through fluids were measured in a high pressure vessel. Ultrasonic transducers were mounted in this vessel and protected from the high pressures by titanium plates. A 20 kHz sonic horn is installed in the cell to provide homogeneous distribution of temperature throughout the solution and also avoid any sub-cooling of the sample that occurs in a non-agitated system.

The acoustic crystallization detection cell was equipped with state of the art temperature and pressure detection tools. To ensure temperature and composition homogeneity, the cell was equipped with a 20 kHz sonic horn. The acoustic cell sat in a controlled temperature chamber, with a circulation system that provided uniform temperature distribution and cooling rates. The cell was equipped with a state of the art data acquisition system.

The experimental apparatus consisted of a fluid velocity cell, an accumulator, a back pressure cell, two pumps and an oven/cooler. The fluid cell was placed in the oven. This allowed the fluid to be measured under identical pressure and temperature conditions. Before putting in any fluid in the velocity cell, the cell and the flow lines were cleaned by flow of methanol and air. The testing brine was then put into the accumulator, and the valve that connects the accumulator and the cell closed. After assembling the cell and flow lines, the valve from the accumulator to the test cell was opened, letting brine flow into the test cell. Pressure and temperature were increased to the desired test level. After the pressure and temperature were stable, the first arrival time data is taken. The pressure is kept constant and the temperature is decreased. When temperature reaches the desired lower level, the data is again taken. The wave signals were digitally recorded, stored, and later analyzed for the first arrival time data. When crystals form in the brine, the arrival time changes. With this change in arrival time, one can detect the brine crystallization temperature at given pressure. The brine solutions were tested for crystallization between 80 to −20° F.

Five clear brine samples, four mud filtrate samples and one mud sample were tested. Table 3 shows the compositions of the clear brine samples. For mud filtrates and mud samples, the compositions are not known.

TABLE 3

| Sample # | wt % NaCl | wt % KCl | wt % CaCl$_2$ | wt % MEG | wt % PAG |
|---|---|---|---|---|---|
| 1 | 10 | 5 | 5 | 5 | 5 |
| 2 | 5 | 5 | 0 | 10 | 10 |
| 3 | 5 | 0 | 5 | 20 | 5 |
| 4 | 15 | 0 | 0 | 10 | 10 |
| 5 | 5 | 5 | 5 | 5 | 5 |

Figure 2:
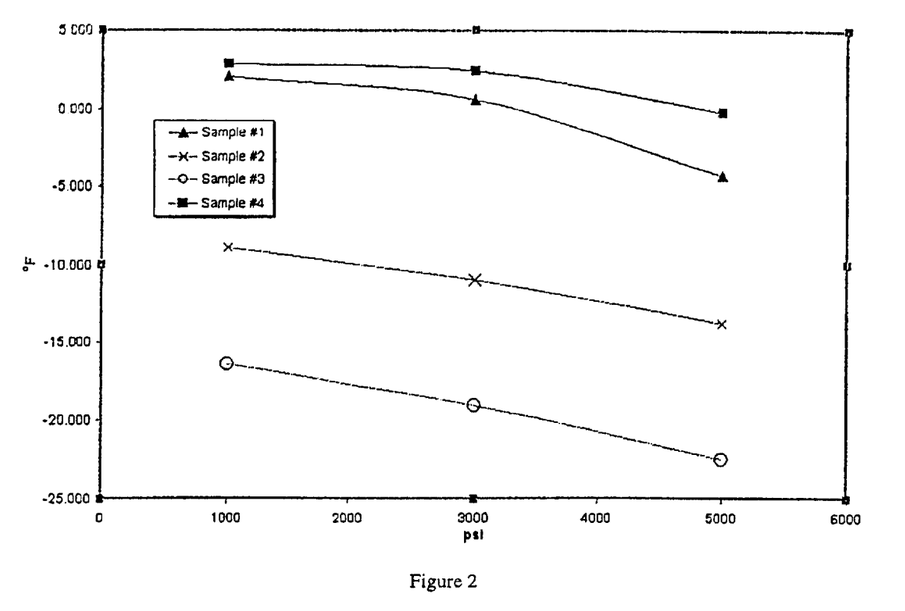
FIG. 2 is a plot of brine crystallization temperature changes with pressure.
Figure 3:
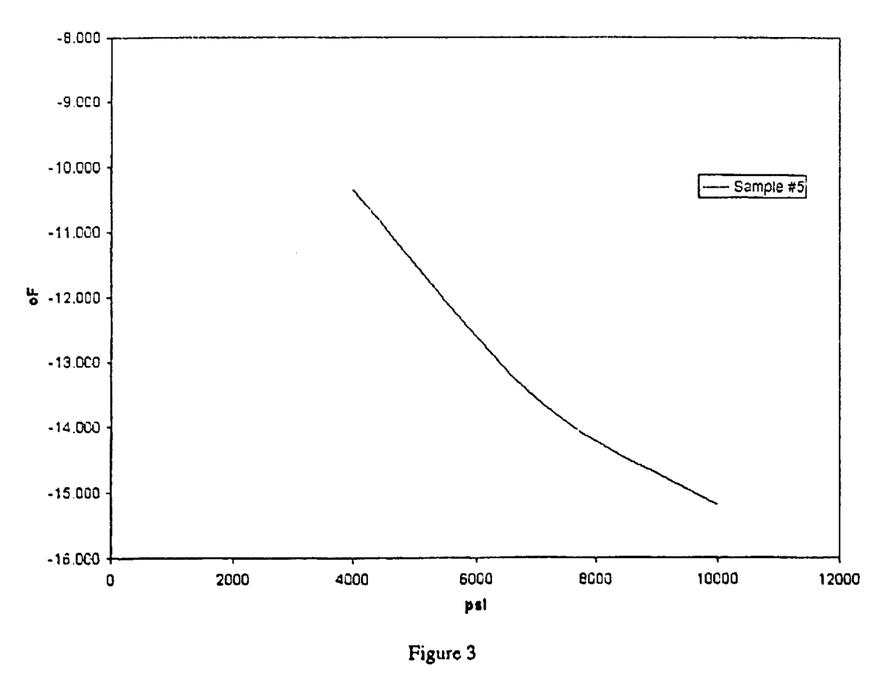
FIG. 3 is a plot of brine crystallization temperature changes with pressure.

Table 4 indicates the test results and FIGS. 2 and 3 the plots. From this table and figures one can see that the more NaCl, MEG and PAG in the brine solution, the lower the crystallization temperature of the brine at a given pressure. It is also interested that for all the brines tested, the crystallization temperature decreased as pressure increases. It should be noted that sample #1 was tested to a higher pressure of 10,000 psi and others only to 5,000 psi.

TABLE 4

| Sample # | Pressure (psi) | P C Temp. (EF) | Pressure (psi) | P C Temp. (EF) | Pressure (psi) | P C Temp. (EF) |
|---|---|---|---|---|---|---|
| 1 | 4000 | −10.3 | 7000 | −13.5 | 10000 | −15.2 |
| 2 | 1000 | 2.0 | 3000 | 0.6 | 5000 | −4.2 |
| 3 | 1000 | −9.0 | 3000 | −11.0 | 5000 | −13.8 |
| 4 | 1000 | −16.4 | 3000 | −19.0 | 5000 | −22.5 |
| 5 | 1000 | 2.8 | 3000 | 2.4 | 5000 | −0.2 |

Sample #1 and #5 have a similar concentration of additives. For #1, the concentration of NaCl is 5% larger than that of #5. However, the crystallization temperature of sample #1 was 10° F. lower than that of sample #5 at 5000 psi, which indicates that higher NaCl concentration will reduce brine crystallization temperature. The same conclusion can be reached when comparing the test results between samples #2 and #4. Even through sample #4 does not have KCl, its overall salt concentration is higher than that of sample #2.

Samples #4 and #5 have the same total salt concentration, but the concentrations of MEG and PAG were double for the sample #4. Results showed that the crystallization temperature was lower for high concentration of MEG and PAG. Also, test results of samples #2 and #3 support this conclusion. The affect of glycol and salt interaction on crystallization temperature at elevated pressure can be understood clearly if more tests are conducted with a series of specified salt and glycol mixing.

For mud filtrate samples, since all samples already has the salt crystal at room temperature and pressure, the increase pressure and decrease temperature did not form new crystals. This may be affected by mud additives in the filtrate to delay the crystal formation. For drilling mud tested, no crystals were detected. Table 5 shows the compositions of the muds. FIGS. 2 and 3 show brine crystallization temperature changes with pressure.

TABLE 5

| Sample #2 | 5 | 7 | 9 |
|---|---|---|---|
| Fresh water (207.88 g) | Water (202.58 g) | Water (169.81 g) | Water (144.15 g) |
| Sea Water (8.72 g) | NaCl (64.75 g) | KCl (45.38 g) | KCl (58.67 g) |
| NaCl (67.78 g) | Caustic soda (0.48 g) | NaCl (22.62 g) | NaCl (29.34 g) |
| Caustic soda (0.35 g) | BP 208 (4.79 g) | Magnesium Oxide (1.0 g) | Sodium silicate (60.05 g) |
| Propylene Glycol (33.89 g) | Propylene Glycol (32.38 g) | Propylene glycol (1.42 g) | Propylene glycol (36.67 g) |
| Poly (Butylene) Glycol (1.69 g) | Petrofree (16.16 g) | Petrofree (14.18 g) | Petrofree (18.34 g) |
| Petrofree (16.95 g) | Drill Thin (0.97 g) | Drill thin (0.85 g) | Drill thin (1.10 g) |
| Drill Thin (1.02 g) | Polybutylene Glycol (1.62 g) | Polybutylene glycol (1.42 g) | Gem 2000 (16.55 g) |
| Soda ash (0.80 g) | Barite (181.44 g) | N Dril HT (4.5 g) | Poly (butylene) glycol (1.83 g) |
| Barite (165.55 g) | Gel (10.0 g) | N Vis P (0.2 g) | Barite (145.38 g) |
| PHPA (1.5 g) | Pac LV (0.5 g) | Drill solids (30.0 g) | Pac LV (0.5 g) |
| Pac LV (1.0 g) | CM Starch (2.50 g) | Baracarb 5 (115.8 g) | CM Starch (5.0 g) |
| CM Starch (1.0 g) | Xan Vis (0.20 g) | Baracarb 50 (115.8 g) | Xan Vis (0.2 g) |
| Prehydrated Gel (10.0 g) | Drill solids (30.0 g) | Drill solids (30.11 g) | Xan Vis (0.1 g) |
| Drill Solids (30.0 g) | | | |

Figure 6:
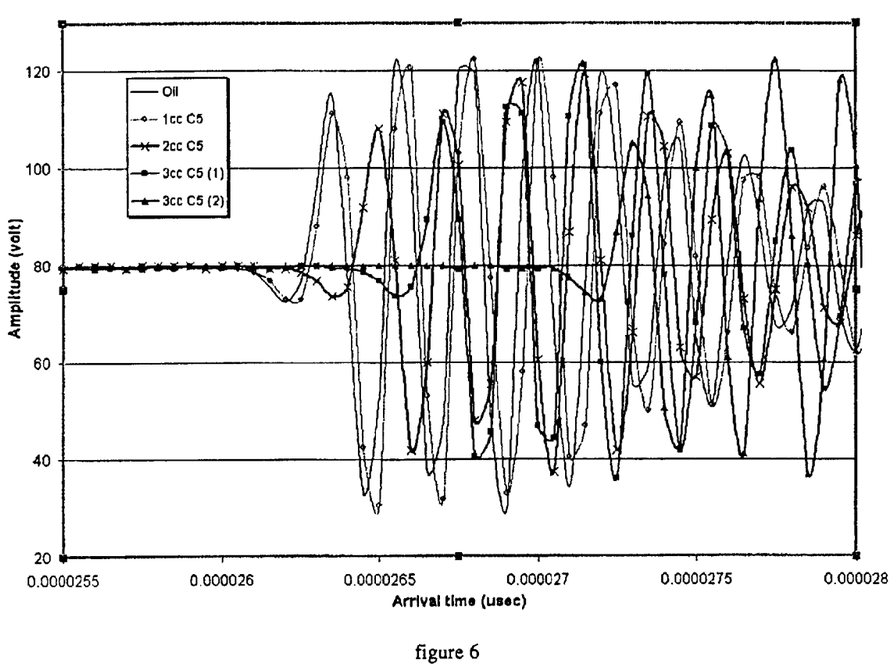
FIG. 6 is a plot of acoustic arrival time vs. signal amplitude for wax/asphaltene detection with mixing.

To further understand the effect of salt and glycol concentration on PCT, five samples were studied having properties as shown in FIG. 6, providing the results listed in Table 7.

TABLE 6

| Sample # | wt % NaCl | wt % KCl | wt % CaCl$_2$ | wt % MEG | wt % PAG |
|---|---|---|---|---|---|
| 2a | 15 | 5 | 0 | 10 | 10 |
| 2b | 0 | 5 | 5 | 10 | 10 |
| 2c | 5 | 0 | 5 | 10 | 10 |
| 3a | 5 | 0 | 5 | 25 | 0 |
| 3b | 5 | 0 | 5 | 10 | 15 |

TABLE 7

| Sample # | Pressure (psi) | P C Temp (° F.) | Pressure (psi) | P C Temp (° F.) | Pressure (psi) | P C Temp (° F.) |
|---|---|---|---|---|---|---|
| 2a | 1000 | No Crystal up to -18° F. | 3000 | No Crystal up to -18° F. | 5000 | No Crystal up to -18° F. |
| 2b | 1000 | 2.03 | 3000 | -.20 | 5000 | -2.43 |
| 2c | 1000 | -3.85 | 3000 | -4.25 | 5000 | -5.47 |
| 3a | 1000 | -14.18 | 3000 | -16.00 | 5000 | -17.62 |
| 3b | 1000 | -5.67 | 3000 | -7.70 | 5000 | -12.76 |

Samples 2a, 2b and 2c were prepared by changing salt concentration in solution 2 in table 5. In solution 2a, increasing NaCl concentration from 5 wt % to 15 wt % decreased the crystallization of the mixture, as no crystals were detected up to -18° F. Replacing NaCl with CaCl$_2$ in sample 2b increased the crystallization temperature. The increase is greater for higher pressure. Replacing KCl with CaCl$_2$ in the solution decreased the crystallization temperature. The following CaCl$_2$ trend was observed for lowering the temperature of crystallization:

$$NaCl > CaCl_2 > KCl.$$

Figure 4:
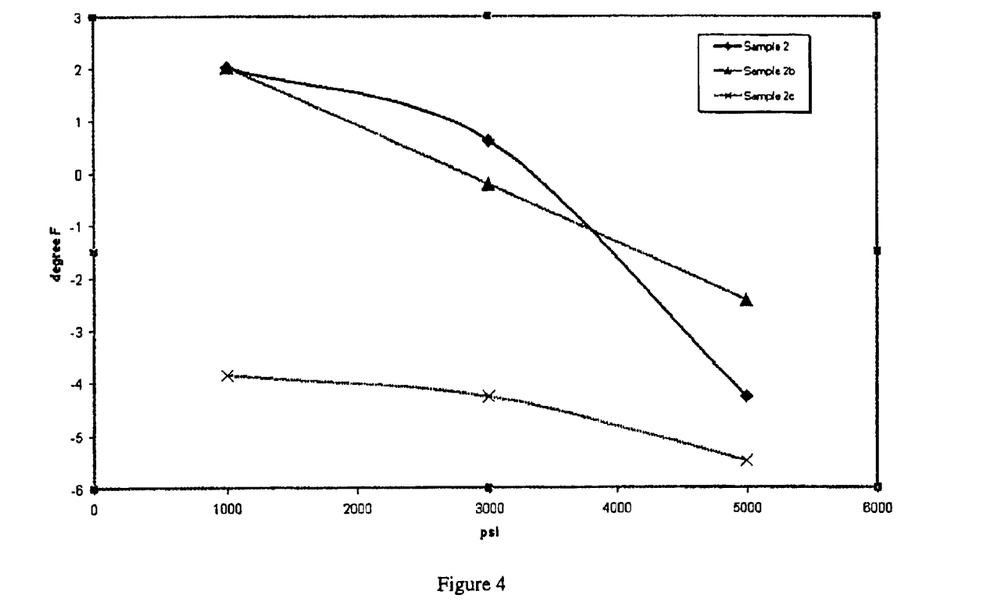
FIG. 4 is plot showing the effect of varying salt concentration.

FIG. 4 shows the effect of salt concentration variations. Samples 3a and 3b were prepared by changing glycol concentration in solution 3 in table 5. Increasing MEG concentration and with no PAG in the mixture, the PCT tends to decrease about 5° F. for each pressure. Decreasing MEG and increasing PAG concentration in the solution tends to increase the PCT. The difference in PCT is higher at lower pressure as compare to higher pressure.

Figure 5:
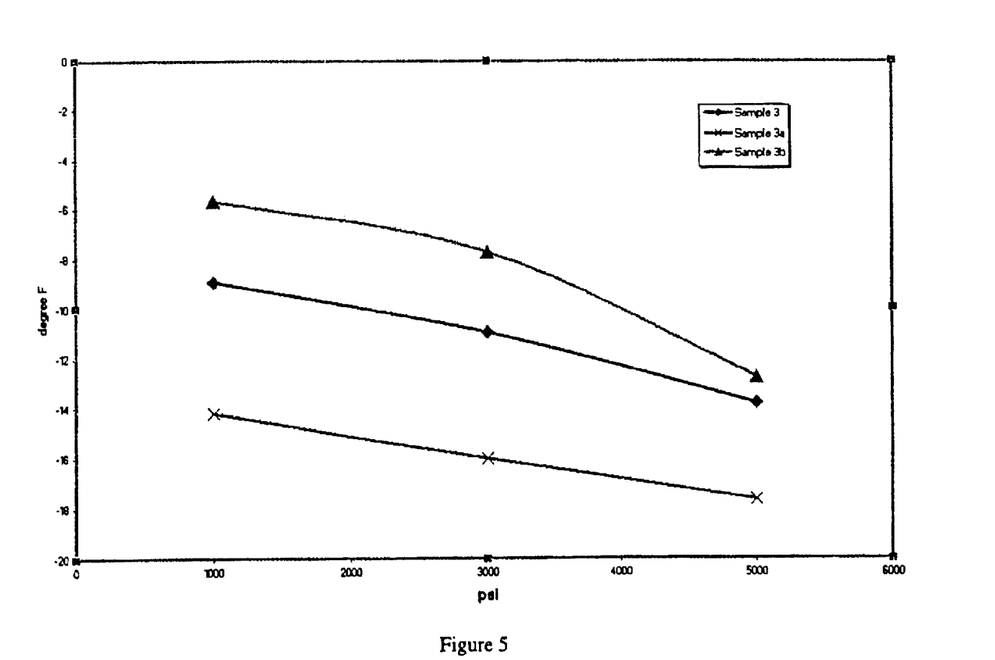
FIG. 5 is a plot showing the effect of varying glycol concentration.

FIG. 5 shows the effect of glycol concentration variations. The second set of hydrate brines shows some contradiction, in the sense that as the salt concentration was increased in sample 2a to 15%NaCl from 5%NaCl in sample 2, the PCT for 2a was expected to be at a higher temperature than for sample 2. Sample 2a did not show any phase change (crystallization) even at about -18° F. This can be explained as a depression of the freezing point for water as the concentration of salt in the mixture is increased. In other words, the crystallization temperature is less that the freezing point temperature for the mixture, i.e. the solution froze before crystallization. This conclusion can be drawn for the entire set of solutions tested.

The mixing provided by the sonic horn was the key factor in the improved testing accuracy for the system. Without proper and continuous mixing of samples, the sampled mixture tends to sub-cool and crystals do not form. Also, the same setup was used to detect the gas-hydrate at high pressure and low temperature, using the 20 kHz horn for effective mixing in a closed system.

The above discussed setup was also used to detect hydrate and wax/asphaltene. The plot of FIG. 6 shows the effectiveness of the mixing horn. During the wax/asphaltene detection, an oil sample was first measured at standard temperature and pressure (STP). Initially 1 cc of pentane was introduced and the system was agitated and measured. Then 1 cc more pentane was added to the system and the sample was again mixed using the sonic horn. When the 1 cc of pentane was added for the third time, some changes were detected in the acoustic signal showing formation of wax/asphaltene appearance. When the sample was agitated using the 20 kHz horn, a significant change in the acoustic signal was observed, indicating the formation of wax/asphaltene in the cell. Wax/asphaltene drops out of the oil at the introduction of 3 cc of pentane to a 35 cc oil sample at STP.

While preferred embodiments of the present invention have been illustrated and discussed in detail, it is apparent that further modifications and adaptations of the preferred embodiments will occur to those skilled in the art. It is to be expressly understood that such modifications and adaptations are included within the spirit and scope of the present invention as set forth in the following claims.

What is claimed is:

1. An acoustic measurement system for detecting solids in a fluid or for measuring the bulk modulus of the fluid comprising:
    a sample cell for containing the fluid;
    a pressurizing line extending from a pump to the sample cell for subjecting fluid within the cell to a variable fluid pressure in excess of 15,000 psi;
    a first acoustic transducer for outputting an acoustic detection signal at a first high frequency to the pressurized sample cell;
    an acoustic receiver responsive to the first acoustic detection signal; and
    a second acoustic transducer for outputting an acoustic mixing signal of a second low frequency to mix any solids in the pressurized fluid within the sample cell.

2. An acoustic measurement system as defined in claim 1, wherein the first acoustic signal has a frequency from 500 kHz to 1 gHz.

3. An acoustic measurement system as defined in claim 2, wherein the second acoustic mixing signal has a frequency of about 50 kHz or less.

4. An acoustic measurement system as defined in claim 1, further comprising:
    a controller for regulating the "on" time of the second transducer, and for detecting the acoustic detection signal during a "off" time of the second transducer.

5. An acoustic measurement system as defined in claim 1, wherein each of the first acoustic transducer and second acoustic transducer is positioned against an internal surface of the cell.

6. An acoustic measurement system as defined in claim 1, further comprising:
    an adjustable controller for selectively altering the frequency of the second acoustic transmitter.

7. An acoustic measurement system as defined in claim 1, further comprising:
    a temperature control device for regulating the temperature of the fluid within the cell.

8. An acoustic measurement system as defined in claim 1, further comprising:
    a pressure sensor for sensing the fluid pressure of fluid in the cell; and
    a temperature sensor for sensing the temperature of fluid in the cell.

9. An acoustic measurement system as defined in claim 1, further comprising:
    a resistivity sensor for sensing the resistivity of fluid in the cell while the fluid is pressurized in excess of 15,000 psi.

10. A acoustic measurement as defined in claim 1, further comprising:
    one or more of an infrared spectroscopy sensor and a video monitor for monitoring the fluid in the cell.

11. An acoustic measurement system for detecting solids in a fluid or for measuring the bulk modulus of the fluid, comprising:
    a sample cell for containing the fluid;
    a pressurizing line for subjecting fluid within the cell to a variable pressure in excess of 15,000 psi;
    a first acoustic transducer for outputting an acoustic detection signal at a first frequency in excess of 500 kHz to the pressurized sample sell;
    an acoustic received responsive to the first acoustic detection signal; and
    a second acoustic transducer for outputting an acoustic mixing signal of a second frequency of less than about 50 kHz to mix any solids in the pressuzed fluid within the sample cell; and
    an adjustable controller for selectively altering the frequency of the second acoustic transducer.

12. An acoustic measurement system as defined in claim 11, further comprising:
    a controller for regulating the "on" time of the second transducer, and for detecting the acoustic detection signal during a "off" time of the second transducer.

13. An acoustic measurement system as defined in claim 11, wherein each of the first acoustic transducer and second acoustic transducer is positioned against an internal surface of the cell.

14. An acoustic measurement system as defined in claim 11, further comprising:
    a temperature control device for regulating the temperature of the fluid within the cell.

15. A method of detecting solids in a fluid or for measuring the bulk modulus of the fluid, comprising:
    providing a sample cell for containing the fluid;
    pressurizing the fluid in the cell to a variable flow pressure in excess of 15,000 psi;
    outputting a first acoustic detection signal at a first frequency to the fluid in the pressurized sample cell;
    providing a detector responsive to the outputted first detection signal; and
    outputting a second acoustic mixing signal at a second frequency to mix any solids in the pressurized fluid within the sample cell.

16. The method as defined in claim 15, further comprising:
    controlling the "on" time of a second transducer, such that the acoustic detection signal is monitored during a "off" time of the second transducer.

17. A method as defined in claim 15, further comprising:
    varying the temperature of a fluid within the sample cell while outputting the first detection signal.

18. The method as defined in claim 15, further comprising:
    detecting crystallization for a portion of the fluid in the test cell in response to the detected acoustic detection signal.

19. The method as defined in claim 13, further comprising:
    adjusting the frequency of the second transducer which outputs the second acoustic mixing signal.

20. The method as defined in claim 13, further comprising:
    operating a first transducer to output the first acoustic detection signal at a frequency of more than about 500 kHz; and
    operating a second transducer to output the second acoustic detection signal at a frequency of less than about 50 kHz.

* * * * *